US010436745B2

(12) United States Patent
Star

(10) Patent No.: US 10,436,745 B2
(45) Date of Patent: Oct. 8, 2019

(54) PH SENSOR SYSTEM AND METHODS OF SENSING PH

(75) Inventor: Alexander Star, Pittsburgh, PA (US)

(73) Assignee: University of Pittsburgh— Of the Commonwealth System of Higher Education, Pittsburgh, PA (US)

(*) Notice: Subject to any disclaimer, the term of this patent is extended or adjusted under 35 U.S.C. 154(b) by 1152 days.

(21) Appl. No.: 14/232,138

(22) PCT Filed: Jul. 11, 2012

(86) PCT No.: PCT/US2012/046259
§ 371 (c)(1),
(2), (4) Date: Mar. 26, 2014

(87) PCT Pub. No.: WO2013/009875
PCT Pub. Date: Jan. 17, 2013

(65) Prior Publication Data
US 2014/0318990 A1    Oct. 30, 2014

Related U.S. Application Data

(60) Provisional application No. 61/507,050, filed on Jul. 12, 2011.

(51) Int. Cl.
*G01N 27/414*        (2006.01)
*G01N 21/80*         (2006.01)
(Continued)

(52) U.S. Cl.
CPC .......... *G01N 27/4146* (2013.01); *B82Y 15/00* (2013.01); *G01N 21/80* (2013.01);
(Continued)

(58) Field of Classification Search
None
See application file for complete search history.

(56) References Cited

U.S. PATENT DOCUMENTS

2002/0085968 A1*  7/2002  Smalley ................. B01J 19/081
                                                428/367
2005/0232844 A1* 10/2005  Diner ..................... B82Y 10/00
                                                423/447.2
(Continued)

FOREIGN PATENT DOCUMENTS

| KR | 100821699 B1    | 4/2008 |
| KR | 102010-0081098 A | 7/2010 |
| WO | WO2013009875 A2 | 1/2013 |

OTHER PUBLICATIONS

Zhang, Wid-De et al, "A Solid-State pH sensor based on WO3-modified vertically aligned multiwalled carbon nanotubes", Mar. 10, 2009, Electrochemistry Communications, 11, 1038-1041 (Year: 2009).*

(Continued)

*Primary Examiner* — Jill A Warden
*Assistant Examiner* — Brittany I Fisher
(74) *Attorney, Agent, or Firm* — Bartony & Associates, LLC

(57) ABSTRACT

A system for measuring pH includes a substrate and a sensor medium on the substrate. The sensor medium includes at least one oxidized carbon nanostructure and optionally at least one composition immobilized on the at least one oxidized carbon nanostructure. The at least one composition has at least one property that depends on pH. The system further includes at least one measurement system to measure a property of the sensor medium.

19 Claims, 15 Drawing Sheets

(51) Int. Cl.
*B82Y 15/00* (2011.01)
*G01N 27/12* (2006.01)
*B82Y 30/00* (2011.01)
*B82Y 99/00* (2011.01)

(52) U.S. Cl.
CPC ............ *G01N 27/128* (2013.01); *B82Y 30/00* (2013.01); *B82Y 99/00* (2013.01); *Y10S 977/75* (2013.01); *Y10S 977/773* (2013.01); *Y10S 977/902* (2013.01)

(56) References Cited

U.S. PATENT DOCUMENTS

| | | | |
|---|---|---|---|
| 2007/0048180 A1* | 3/2007 | Gabriel | B82Y 15/00 422/400 |
| 2007/0048181 A1* | 3/2007 | Chang | B82Y 15/00 422/400 |
| 2008/0021339 A1* | 1/2008 | Gabriel | A61B 5/0833 600/532 |
| 2008/0035481 A1 | 2/2008 | McCormack | |
| 2008/0199904 A1* | 8/2008 | Suslick | C12Q 1/04 435/34 |
| 2010/0056892 A1* | 3/2010 | Ben-Barak | A61B 5/073 600/354 |
| 2010/0159366 A1* | 6/2010 | Shao-Horn | H01G 11/36 429/532 |
| 2010/0252450 A1* | 10/2010 | Riehl | B82Y 15/00 205/775 |
| 2011/0127446 A1 | 6/2011 | Star | |
| 2012/0116683 A1* | 5/2012 | Potyrailo | G01N 27/02 702/19 |

OTHER PUBLICATIONS

Chen, Changlun et al, "Oxygen Functionalization of Multiwall Carbon Nanotubes by Microwave-Excited Surface-Wave Plasma Treatment", Apr. 14, 2009, Journal of Physical Chemistry, vol. 113, No. 18, 7659-7665 (Year: 2009).*

Anglada-Ferrer, N et al, "Transparent and flexible carbon nanotubes/polypyrrole and carbon nanotube/polyaniline pH sensors", Oct. 2, 2006, Physica Status Solidi (b), 243, 3519-3523 (Year: 2006).*

Chauhan, Nidhi et al.; An amperometric biosensor based on acetylcholinesterase immobilized onto iron oxide nanoparticles/multi-walled carbon nanotubes modified gold electrode for measurement of organophosphorus insecticides; Analytica Chimica Acta 701 (2011) 66-74.

Cui, Yi et al., Nanowire Nanosensors for Highly Sensitive and Selective Detection of Biological and Chemical Species, Science, vol. 293 (2001), pp. 1289-1292.

* cited by examiner

Figure 1A
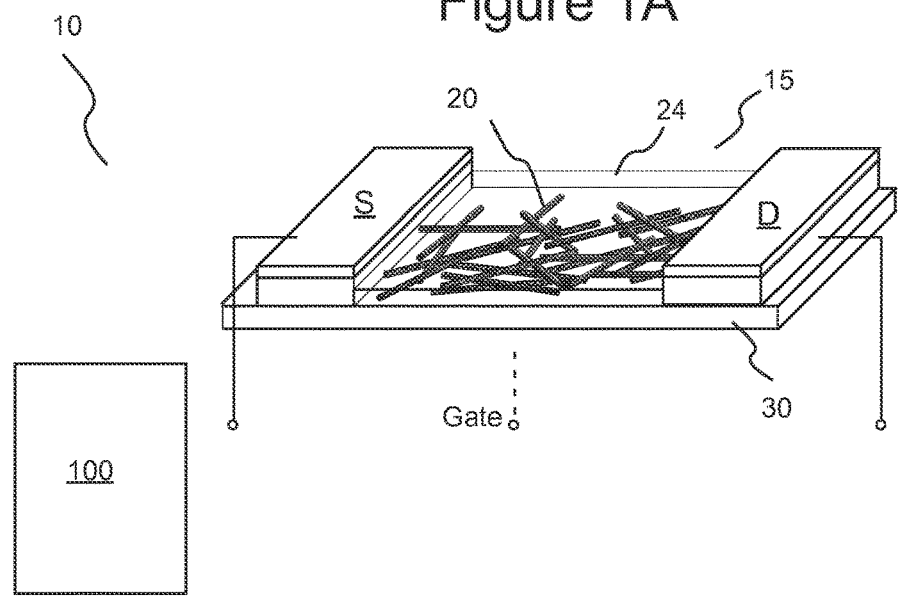
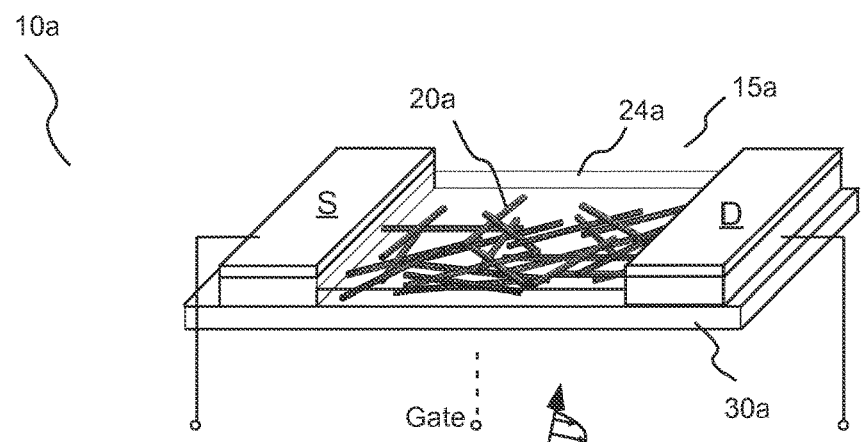
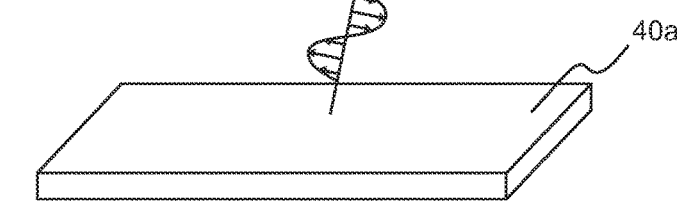
Figure 1B

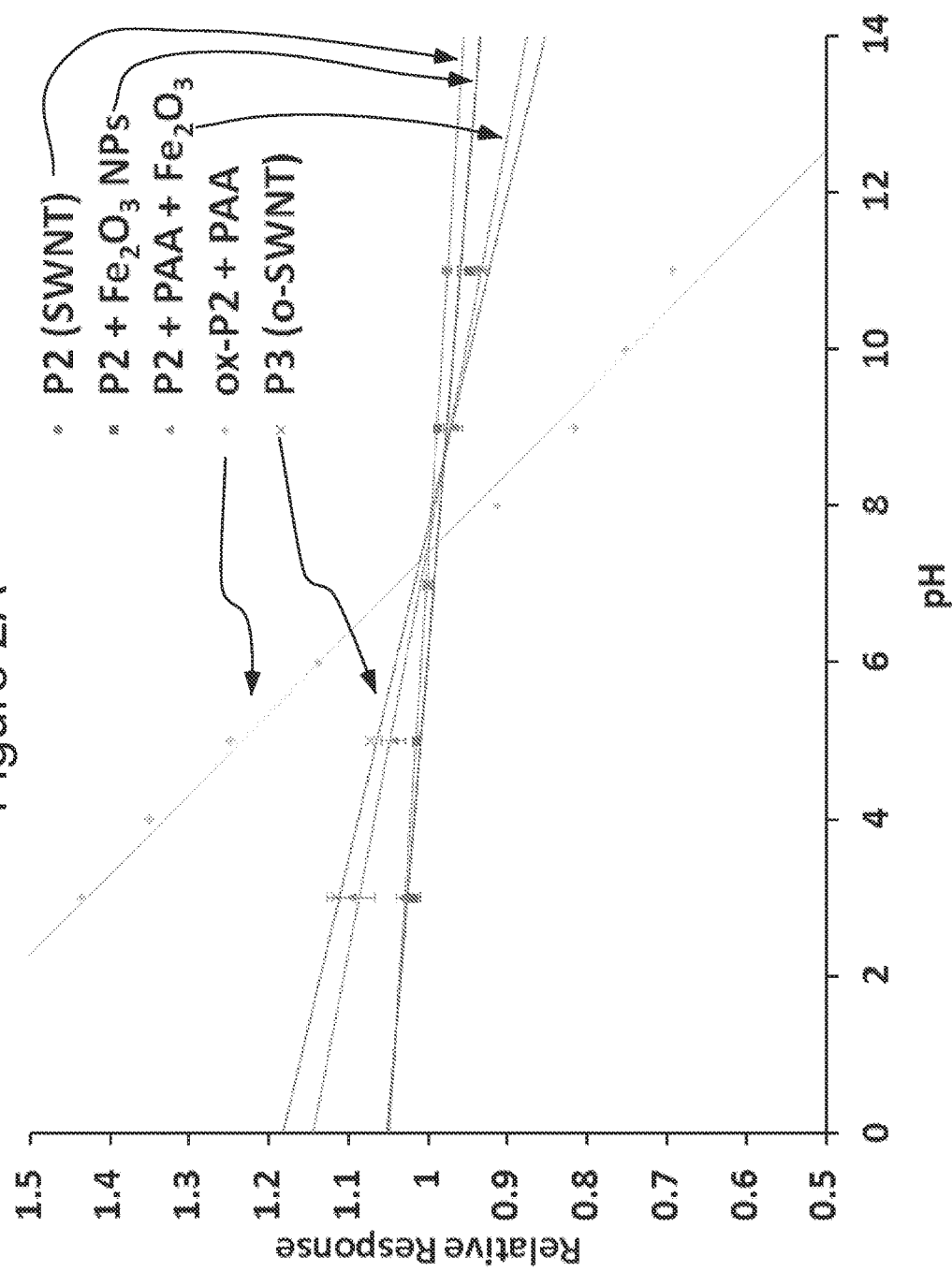

PH SENSOR SYSTEM AND METHODS OF SENSING PH

CROSS-REFERENCE TO RELATED APPLICATIONS

This application is a 35 U.S.C. 371 National Phase application of International PCT Patent Application number PCT/US2012/046259, filed Jul. 11, 2012 which claims benefit of U.S. Provisional Patent Application Ser. No. 61/507,050, filed Jul. 12, 2011, the disclosures of which are incorporated herein by reference.

GOVERNMENTAL INTEREST

This invention was made with government support under grant no. DE-FE-0004000 awarded by the Department of Energy. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Aqueous solutions receive a lot of attention as water covers over seventy percent of the planet and is vital for all known forms of life. In water, hydrogen atoms constantly transfer from one water molecule to another forming two charged species: the hydroxide ion ($OH^-$) and the hydronium ion ($H_3O^+$). While the relative concentrations of these two ions can vary, their product remains constant. Addition of foreign species, such as an acid or a base, can adjust the ratio of these two ions. The pH scale, a log concentration scale, has been developed to define such solutions, which is related to the concentration of hydronium ions by $pH=-\log[H_3O^+]$. The pH of a solution can have a significant effect on chemical processes, therefore both the measurement and control of pH is important for materials, life, and environmental sciences. For example, it would be beneficial to monitor the pH inside the human body. However, such monitoring is very difficult with conventional technologies. Additionally, pH sensors may be exposed to extraordinary conditions, such as extreme temperature and pressure, in applications such as geochemistry for monitoring pH levels inside the earth's ocean to facilitate carbon sequestration technologies. Once again, such monitoring is very difficult with conventional technologies.

The most common pH sensors are glass electrodes with a salt solution-filled glass membrane limiting their applications. Some common problems associated with such electrodes include temperature dependence and errors in measurement in intense conditions (i.e., low pH and low ionic-strength solutions).[1] Additionally, glass pH electrodes become sensitive to alkali-metal ions at high pH, degrade if dehydrated, and require calibration with a standard buffer (potentially introducing associated errors).

The field of ion-selective field-effect transistors (ISFETs) which started more than 40 years ago has promised development of rugged, small, rapid response pH sensor devices. Additionally, ISFETs would not require hydration and would be inert toward harsh environments. While there are numerous advantages of using ISFETs, one major limitation of the technology involves the requirement of a reference electrode, ultimately limiting the ability to reduce their size.

SUMMARY

In one aspect, a system for measuring pH includes a substrate and a sensor medium on the substrate. The sensor medium includes at least one oxidized carbon nanostructure and optionally at least one composition immobilized on the at least one oxidized carbon nanostructure. The at least one composition has at least one property that depends on pH. The system further includes at least one measurement system to measure a property of the sensor medium.

The system may further include a first conductive terminal in electrical connection with the sensing medium and a second conductive terminal in electrical connection with the sensing medium and spaced from the first conductive terminal. In a number of embodiments, the system operates as a chemiresistor. The at least one measurement system may, for example, measure at least one electrical property of the sensor medium.

In a number of embodiments, the at least one measurement system measures at least one optical property of the sensor medium.

In a number of embodiments the sensor medium includes at least one composition immobilized on a network of oxidized carbon nanostructures. The at least one composition may, for example, be immobilized on a network of single-walled carbon nanotubes. In a number of embodiments, the oxidized carbon nanostructures are oxidized to provide a loading of carboxylic groups within the range of approximately 1-20 µmol/mg or within the range of approximately 10-15 µmol/mg. In a number of embodiments, the oxidized carbon nanostructures are oxidized to provide a loading of carboxylic groups of approximately 12 µmol/mg.

The at least one composition may for example, include a polymer. In a number of embodiments, the polymer is a conductive polymer. The conductive polymer may, for example, be a polyaminoanthracene, a polyaniline, a polypyrrole or a derivative thereof. In a number of embodiments, the conductive polymer is a polyaminoanthracene. The polymer may, for example, be poly(ethylene imine), sulfonated tetrafluoroethylene, or poly(sodium 4-styrenesulfonate). In a number of embodiments, the polymer includes functional groups sensitive to H+ concentration. In a number of embodiments, the polymer forms a proton exchange membrane.

In a number of embodiments, the at least one composition includes a metal oxide. The composition may, for example, include metal oxide nanoparticles. The metal oxide nanoparticles may, for example, include at least one of $Fe_2O_3$, $Nd_2O_3$, $WO_3$, $TiO_2$, and $Al_2O_3$.

In another aspect, a system for measuring pH includes a substrate and a sensor medium on the substrate. The sensor medium includes at least one carbon nanostructure and optionally at least one composition immobilized of the at least one carbon nanostructure. The at least one composition has at least one property that depends on pH. The system further includes a first conductive terminal in electrical connection with the sensing medium and a second conductive terminal in electrical connection with the sensing medium and spaced from the first conductive terminal to form a chemiresistor. The system also includes at least one measurement system to measure an electrical property of the sensing medium and relate the measured electrical property to pH.

The sensor medium may, for example, include at least one oxidized carbon nanostructure and optionally at least one composition immobilized on the at least one oxidized carbon nanostructure. In a number of embodiments, the at least one composition is immobilized on a network of oxidized carbon nanostructures. The at least one composition may, for example, be immobilized on a network of single-walled carbon nanotubes. The oxidized carbon nanostructures may, for example, be oxidized to provide a loading of carboxylic groups within the range of approximately 1-20 µmol/mg or within the range of approximately 10-15 µmol/mg. In a number of embodiments, the oxidized carbon nanostructures are oxidized to provide a loading of carboxylic groups of approximately 12 µmol/mg.

The at least one composition may, for example, includes a polymer. The polymer may, for example, be a conductive polymer. The conductive polymer may, for example, be a polyaminoanthracene, a polyaniline, a polypyrrole or a derivative thereof. In a number of embodiments, the conductive polymer is a polyaminoanthracene. The polymer may, for example, be poly(ethylene imine), sulfonated tetrafluoroethylene, or poly(sodium 4-styrenesulfonate). In a number of embodiments, the polymer includes functional groups sensitive to H+ concentration. In a number of embodiments, the polymer forms a proton exchange membrane.

The at least one composition may, for example, include a metal oxide. In a number of embodiments, the composition includes metal oxide nanoparticles. The metal oxide nanoparticles may, for example, include at least one of $Fe_2O_3$, $Nd_2O_3$, $WO_3$, $TiO_2$, and $Al_2O_3$.

In another aspect, a method for measuring pH of an aqueous sample includes placing a system in fluid connection with the aqueous sample. The system includes a substrate and a sensor medium on the substrate. The sensor medium includes at least one oxidized carbon nanostructure and optionally at least one composition immobilized on the at least one oxidized carbon nanostructure. The at least one composition has at least one property that depends on pH. The method further includes measuring at least one property of the sensor medium and relating a measured value of the at least one property of the sensor medium to pH.

In a further aspect, method for measuring pH includes placing a system in fluid connection with the aqueous sample. The system includes a substrate and a sensor medium on the substrate. The sensor medium includes at least one carbon nanostructure and optionally at least one composition immobilized of the at least one carbon nanostructure. The at least one composition has at least one property that depends on pH. The system further includes a first conductive terminal in electrical connection with the sensor medium and a second conductive terminal in electrical connection with the sensor medium and spaced from the first conductive terminal to form a chemiresistor. The method further includes a measuring at least one electrical property of the sensor medium and relating a measured value of the electrical property of the sensor medium to pH.

In still a further aspect, a system for measuring pH includes a sensor medium on the substrate. The sensor medium includes at least one nanostructure and optionally at least one composition immobilized of the at least one nanostructure. The at least one composition has at least one property that depends on pH. The system further includes a first conductive terminal in electrical connection with the sensing medium and a second conductive terminal in electrical connection with the sensing medium and spaced from the first conductive terminal to form a chemiresistor. The system also includes at least one measurement system to measure an electrical property of the sensing medium and relate the measured electrical property to pH.

The devices, systems, methods and compositions hereof alleviate a number of problems associated with currently available pH sensors. For example, two-terminal, chemiresistor systems hereof require measurement of only an electrical property such as the resistance/conductance of the sensor medium bridging the terminals as a function of ion concentration, making measurement relatively easy. Moreover, the low-cost, rugged properties of nanostructure-based sensors and the excellent electronic properties of, for example, single-walled carbon nanotubes or SWNTs provide for the fabrication of stable, miniaturized pH sensors. The use of a reference electrode is not required in the devices, systems and methods hereof.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 1A illustrates schematically an embodiment of a sensor system hereof.

FIG. 1B illustrates an embodiment of a sensor system hereof in which optical properties of nanostructures are measured.

FIG. 2A illustrates the results of studies of the pH sensitivities of a number of different types of single-walled carbon nanotubes (SWNT).

DETAILED DESCRIPTION

Figure 1C:
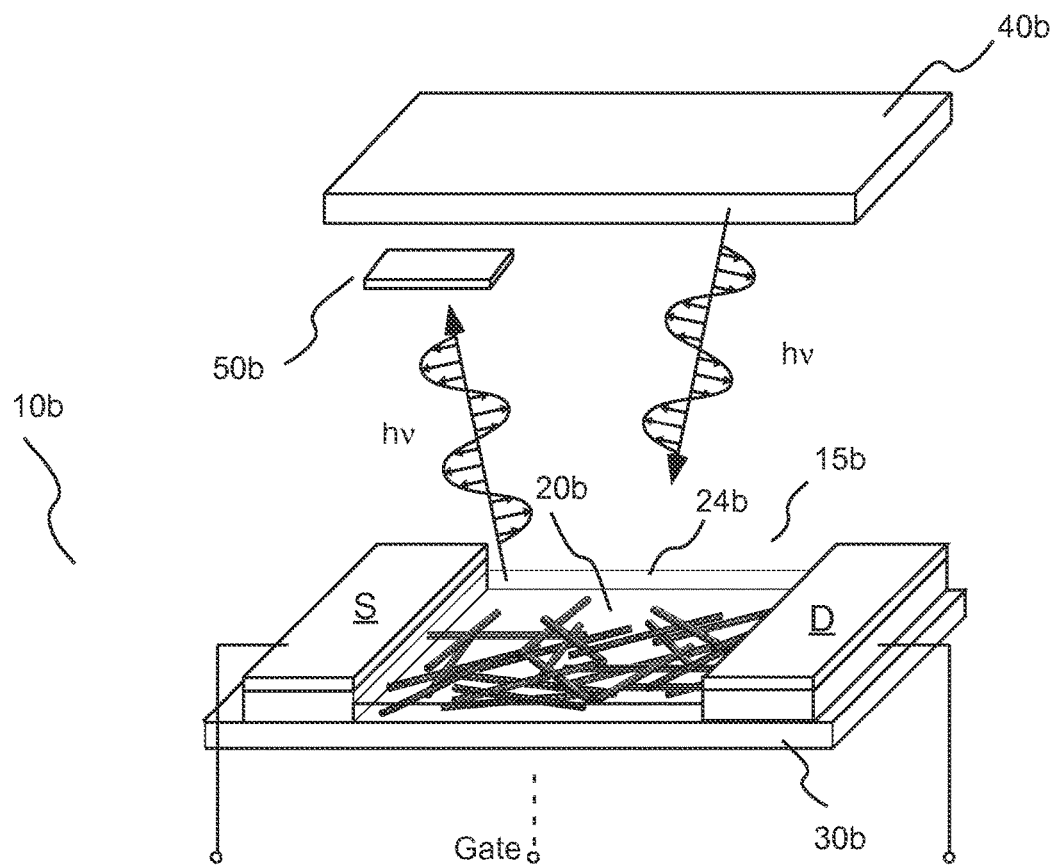
FIG. 1C illustrates an embodiment of a sensor system hereof wherein emission spectroscopy is used to measure optical properties of nanostructures.

As used herein and in the appended claims, the singular forms "a," "an", and "the" include plural references unless the context clearly dictates otherwise. Thus, for example, reference to "an immobilized composition" includes a plurality of such immobilized compositions and equivalents thereof known to those skilled in the art, and so forth, and reference to "the immobilized composition" is a reference to one or more such immobilized compositions and equivalents thereof known to those skilled in the art, and so forth.

In a number of representative embodiments hereof, nanostructures (for example, carbon nanotubes) were used in a sensor medium in two-terminal devices or systems in which the nanotube structures formed a conductive pathway between two terminals which were separated in space. In general, nanostructures have at least one dimension smaller than 100 nm. For example, in a number of embodiments, chemiresistors based on carbon nanotubes required only measurement of, for example, the resistance of the nanostructures as a function of ion concentration, making measurement relatively easy. The low-cost, rugged properties of nanostructure-based sensors and the excellent electronic properties of, for example, single-walled carbon nanotubes (SWNTs) provide stable, miniaturized pH sensors (for example, microsensors). SWNTs are high aspect nanomaterials or nanostructures with diameters of few nanometers (nanoscale) and lengths up to several micrometers (microscale). In a number of embodiment hereof, networks of SWNTs, are used, which are microscale objects. The small sensor size, simplicity of measurement (for example, using a simple meter) and wafer-scale manufacturability of pH sensor hereof are important advantages compared to prior pH sensors. pH sensors hereof may, for example, be incorporated in microelectromechanical systems (MEMS). The pH sensors hereof may, for example, be used in many different environments, including, for example, in implantable systems in which one or more pH sensors hereof are implanted or inserted within a living organism.

In a number of embodiments hereof, pH sensors or systems for measuring pH include a sensor medium including nanostructures as described above and at least one composition immobilized on the nanostructures. The immobilized composition has a property or properties that depend on pH. The pH sensors or systems further include at least one measurement system to measure at least one property of the sensor medium (wherein the at least one property of the sensor medium varies as a function of pH variance). The property or properties measured can, for example, be electrical properties or optical properties. In a number of embodiments, relatively low-cost sensors include at least one measurement system to measure at least one electrical property of the nanostructures (for example, an electrical property related to the conductance/resistance thereof).

As also described above, the system may further include a first terminal or electrode (that is, an electrical conductor used to make contact with the nanostructures/sensor medium) in electrical connection with the nanostructures/sensor medium and a second terminal or electrode in electrical connection with the nanostructures/sensor medium and spaced from the first electrode. The measurement system can, for example, be in electrical connection with the first terminal/electrode and the second terminal/electrode to measure at least one electrical property of the nanostructures/sensor medium related to the resistance/conductance thereof. The measurement system may, for example, include a meter to measure resistance or conductance.

A schematic illustration of a representative embodiment of a sensor system 10 is set forth in FIG. 1A. Illustrated sensor system 10 includes a sensor medium including one or more representative nanostructures including, for example, single-wall carbon nanotubes or SWNTs (for example, a network of SWNTs). As clear to those skilled in the art, various other nanostructures are suitable for use in the present invention. Such nanostructures include, for example, multiple-wall nanotubes, nanowires, nanofibers, nanorods, nanospheres, graphene, or the like, or mixtures of such nano structures. Moreover, in addition to carbon, those skilled in the art will appreciate that the nanostructures of the present invention can be formed of boron, boron nitride, and carbon boron nitride, silicon, germanium, gallium nitride, zinc oxide, indium phosphide, molybdenum disulphide, gold, silver, and/or other suitable materials. Carbon nanotubes, for example, provide a very stable platform for the sensor medium hereof.

As discussed further below, in a number of embodiments, a sensor medium 15 including semiconducting oxidized carbon single-walled nanotubes (o-SWNT) or a network of o-SWNTs 20 (or other nanostructures) is, for example, disposed upon a substrate 30 (for example, a silicon chip) and contacted by two conductive (for example, including a conductive metal such as gold (Au)), spaced terminals or electrodes representing a source (S) and a drain (D). Sensor medium 15 may further include a functionalizing material or layer 24 of a pH sensitive material (for example, a polymer, metal oxide nanoparticles, or mixtures of such materials) immobilized or coated upon SWNT material 20. In a number of embodiments, the polymer is a conductive polymer or other polymer that is sensitive to or has at least one property dependent upon pH. A number of such polymers include functional groups such as amine groups which are sensitive to pH or H+ concentration.

In single-walled carbon nanotubes, all carbon atoms are located on the surface where current flows, making a stable conduction channel that is extremely sensitive to a surrounding chemical environment. Nanotubes, including SWNT's, have the ability to, for example, change resistance/conductance in response to interaction with layer 24. This characteristic is, for example, implemented in system 10. A measurement system 100 is in electrical connection with source (S) and drain (D) to measure at least one electrical property of the nanostructures related to the conductance thereof. Support 30 can, for example, be $SiO_2$, $Si/SiO_2$, or an optically transparent, insulating layer of quartz in a FET-configured or chemiresistor circuit. As an aqueous solution comes into contact with the device surface, SWNT conductance is modified as a function of pH of the aqueous solution to produce a detection signal.

In NTFET (nanotube field-effect transistor) devices, one, for example, measures electrical current through carbon nanotubes under an applied gate voltage. In chemiresistor devices, a gate voltage is not applied. In both types of devices or systems in the systems hereof, electrical conductance (or resistance) of nanostructures changes upon changing pH, thereby providing a sensor signal. Depending on the semiconducting nature of the nanostructures, application of a gate voltage can provide amplification of the sensor signal. Nanostructures such as single-walled carbon nanotubes (SWNTs) are suitable for incorporation into very small and low power devices because they demonstrate significant environmental sensitivity, high electrical conductivity, and inherent compatibility with existing microelectronic fabrication techniques. Moreover, the very small sensor systems hereof may be used in connection with a very small volume of a sample to be monitored.

In several embodiments (such as representative embodiment 10a, illustrated schematically in FIG. 1B) in which optical properties of a sensor medium 15a including nanostructures 20a are to be measured, energy is transmitted through an optically transparent quartz support 30a from an energy source 40a. A transparent substrate is, for example, suitable for absorbance spectroscopy. In the illustrated embodiment, an optical sensor 50a is illustrated schematically.

Alternatively, emission spectroscopy can be employed. As illustrated in system 10b of FIG. 1C, in emission spectroscopy, energy from energy source 40b can be transmitted to layer 24b of sensor medium 15b directly (from above, in the orientation of FIG. 1C), enabling the fabrication of microelectronic chemiresistor or field effect transistors (FETs) devices on opaque supports such as $SiO_2$ for chemiresistors or $Si/SiO_2$ for FETs. An optical sensor 50b measure emitted energy. Emission spectroscopy may, for example, be more sensitive to pH than absorption spectroscopy.

Measurements made with devices or systems including random networks of SWNTs can be advantageous because random network devices are less prone to failure as a result of a large number of conduction pathways. Additionally, while random network devices may not provide information on individual nanotube response, as with singly isolated SWNT FETs, they possess an intrinsic averaging effect in that they remove nanotube-to-nanotube variation as a result of the combined response of the entire network.

A number of representative embodiments and studies hereof, pH sensor system 10 is operated, for example, as a chemiresistor (which includes only two terminals/electrodes) and electrical properties of oxidized single-walled carbon nanotubes having a pH sensitive polymer immobilized thereon are measured. In that regard, to enhance specificity to hydronium ions ($H_3O^+$), carbon nanostructures (nanotubes) were functionalized with a conducting polymer in a number of representative embodiments hereof. The electrical properties of conductive polymers depend on their protonation and can exhibit very fast response when the sensing process occurs on the surface of the polymer. However, a major problem of all organic conductors is their limited chemical stability. Nanostructure such as carbon nanotubes can help to stabilize polymers, increasing the lifetime of a sensor system, while additionally increasing the aspect ratio of the polymer for facile integration into, for example, micrometer sized electronics. Combining the two types of materials provided synergetic effects in the pH sensor systems hereof. The polymer contributes to the device selectivity, while the nanostructures provide a sensitive and robust platform necessary to chemically stabilize the polymer. In a number of representative studies, a pH sensitive system was formed by combining oxidized SWNTs (o-SWNTs) with a conducting polymer, poly(1-aminoanthracene) (PAA).

The systems hereof do not require the use of a reference electrode for sensing pH. The pH levels may be monitored electrically by configuring the nanotube/functionalizing layer composite as, for example, a chemiresistor as well as optically by depositing a film onto, for example, a quartz plate as described above. The conductance of the nanostructure network (for example, a PAA/o-SWNT network) changes linearly with respect to the concentration of hydronium ions in solution. Additionally the absorption of the $S_{11}$ electronic transition of a PAA/o-SWNT film is influenced by the presence of acidic (HCl) or basic ($NH_3$) gases. The low-cost, extremely small size, and sensitivity of the system hereof provide for low-cost solid-state pH sensor devices and systems.

FIG. 2A illustrates the results of studies of the pH sensitivities of a number of different types of single-walled carbon nanotubes (SWNTs). As illustrated in FIG. 1, bare, unfunctionalized SWNTs (P2 SWNTs available from Carbon Solutions, Inc.) show minimal sensitivity toward varying pH solutions. Commercially available oxidized SWNTs or o-SWNTs (P3 o-SWNTs available from Carbon Solutions, Inc.) exhibited substantially greater sensitivity toward varying pH solutions. P2 SWNTs functionalized with either metal oxide NPs or with a pH sensitive polymer (PAA) increased the response of the systems to pH, but the increased sensitivities were not as great as the sensitivity exhibited by oxidized SWNTs (P3 o-SWNT). A very large increase in response was attained by doping oxidized SWNTs with a pH sensitive polymer, poly(1-amino anthracene) as represented by ox-P2+PAA in FIG. 1. In that regard, P2 SWNTs were acid treated to form a desired amount of oxygen functionalities thereon and then functionalized with PAA. The pH sensitivity of the ox-P2+PAA material was greatly increased over the wide pH range.

Figure 2C:
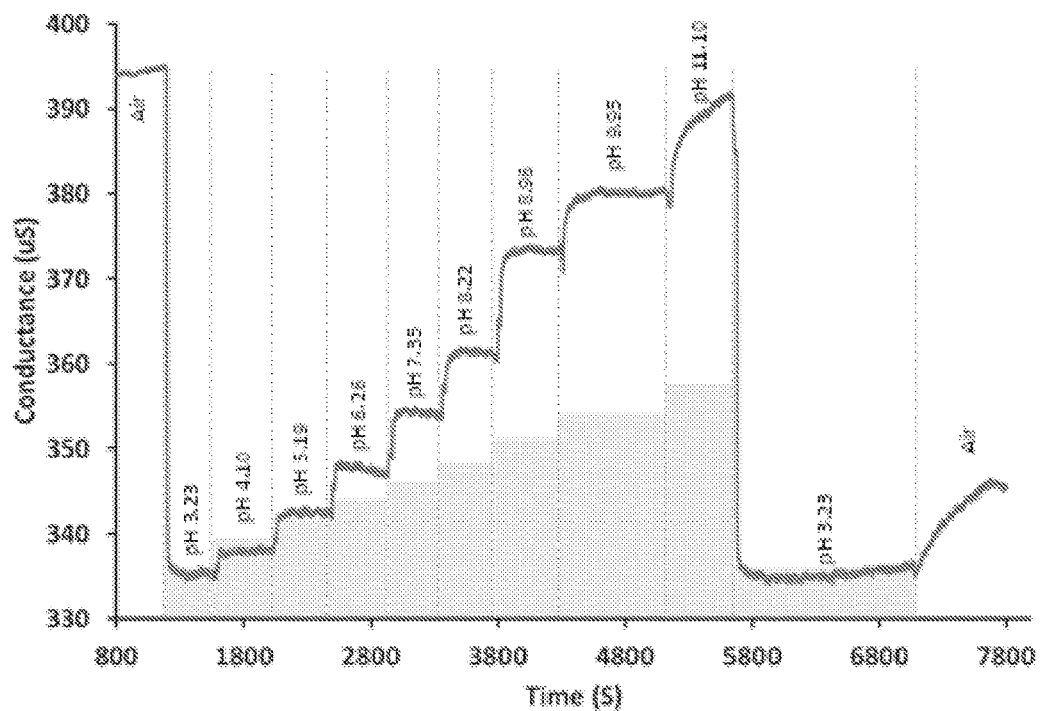
FIG. 2C illustrates conductance as a function of time at various levels of pH for SWNT networks including immobilized iron oxide nanoparticles.
Figure 2B:
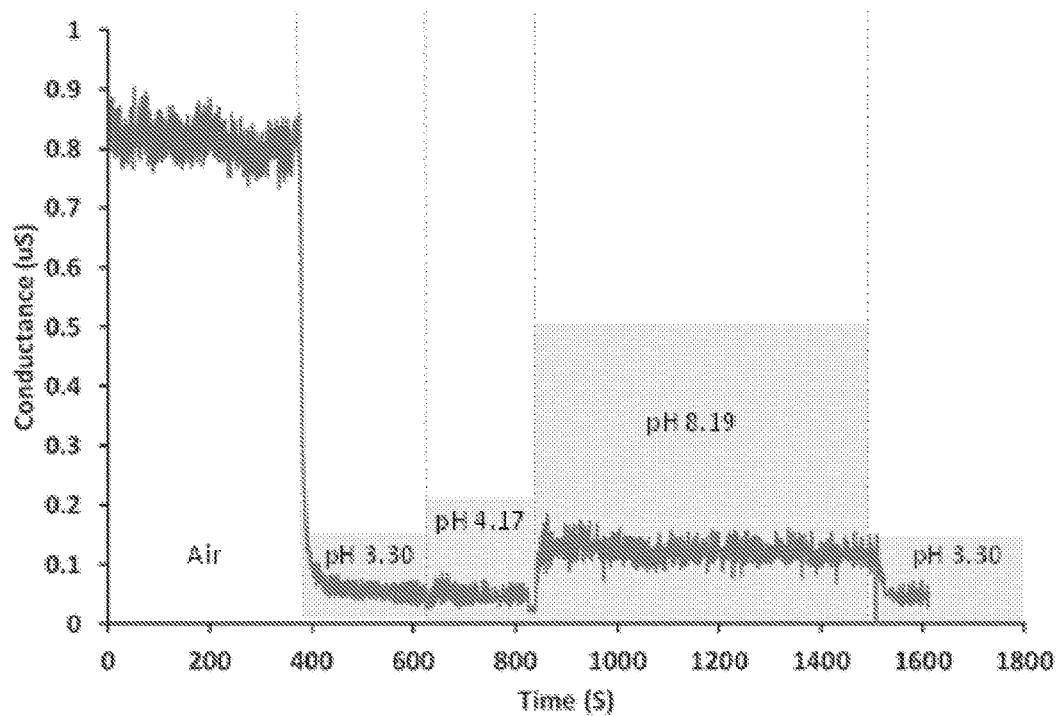
FIG. 2B illustrates conductance as a function of time at various levels of pH for SWNT networks configured as a chemiresistor.

FIGS. 2B and 2C illustrate the use of metal oxide nanoparticles immobilized on SWNT. In that regard, FIGS. 2B and 2C illustrate conductance as a function of time for SWNT networks configured as a chemiresistor. As illustrated in FIG. 2B, bare SWNTs show only slight sensitivity toward pH. However, as illustrated in FIG. 2C, addition of iron oxide nanoparticles increases the response significantly. Without limitation to any mechanism, the increase in response may be attributable to electrostatic gating based on the inherent pH sensitivity of metal oxide nanoparticles. Metal oxide nanoparticles that give increased pH sensitivity include, but are not limited to, $Fe_2O_3$, $Nd_2O_3$, $WO_3$, $TiO_2$, and $Al_2O_3$. In immobilizing metal oxide nanoparticles on nanostructures, the metal oxide nanoparticles may, for example, be first dispersed in any number of solvents (for example, acetone) and then deposited on the device surface (SWNT networks) by drop-casting. Other deposition methods, including, for example, spin-coating, dipping, microspotting, etc. are also possible.

Figure 3A:
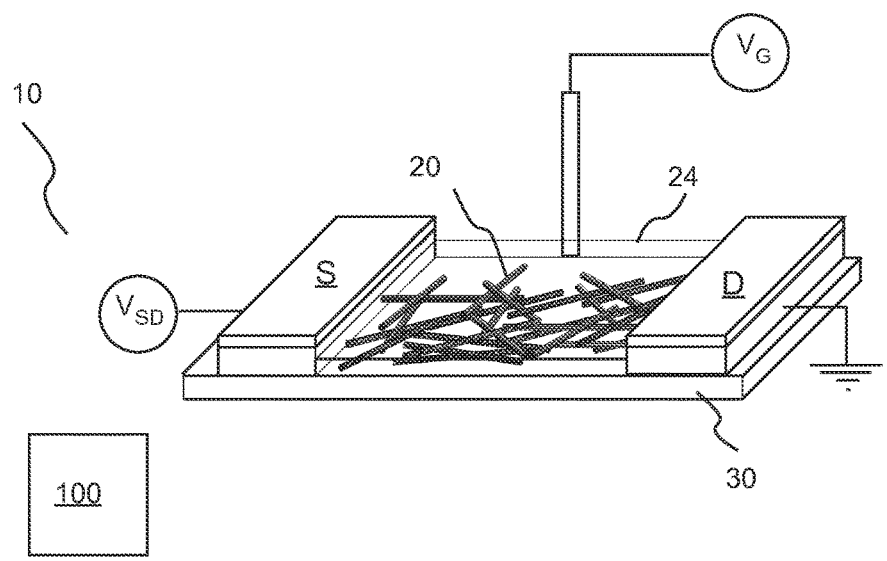
FIG. 3A illustrates schematically a system for effecting field-effect transistor (FET) measurements.
Figure 3B:
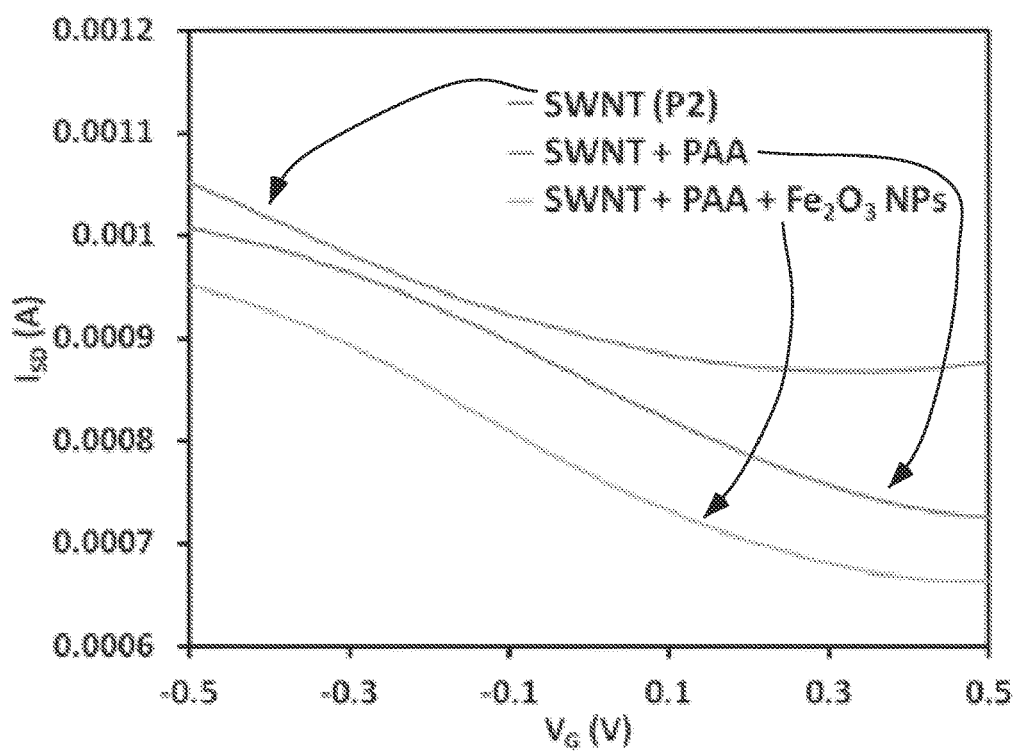
FIG. 3B illustrates current as a function of gate voltage for SWNT, SWNT including immobilized poly(1-aminoanthracene) (PAA) and SWNT including immobilized PAA and $Fe_2O_3$ nanoparticles.
Figure 3C:
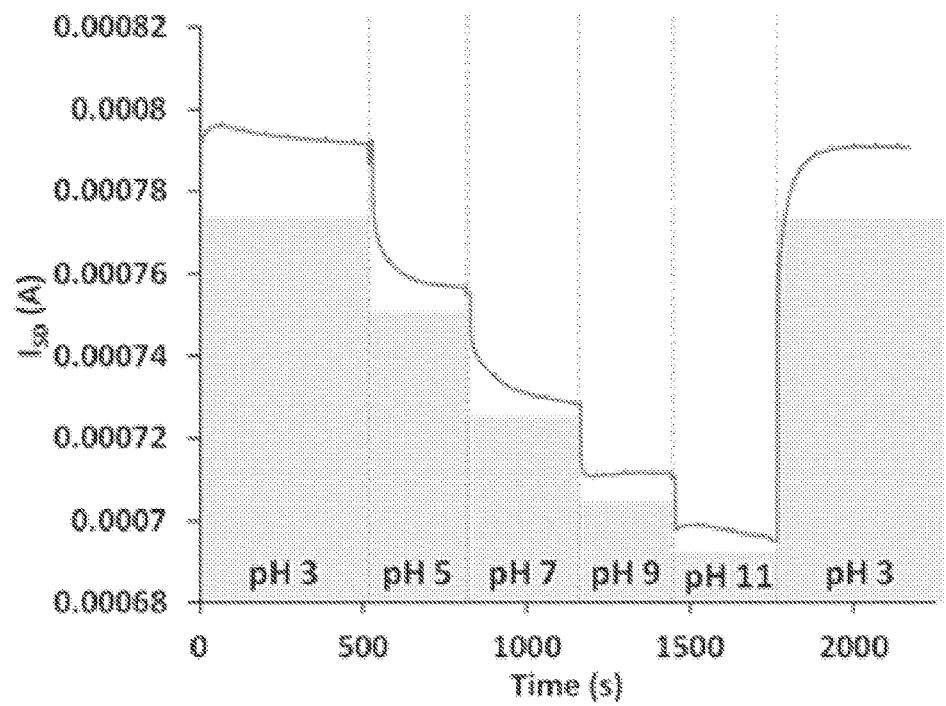
FIG. 3C illustrates a plot of current versus time for a system hereof functionalized by dropcasting SWNTs, electropolymerizing PAA, and then dropcasting $Fe_2O_3$ nanoparticles without applying a gate voltage, when exposed to various pH solutions.
Figure 3D:
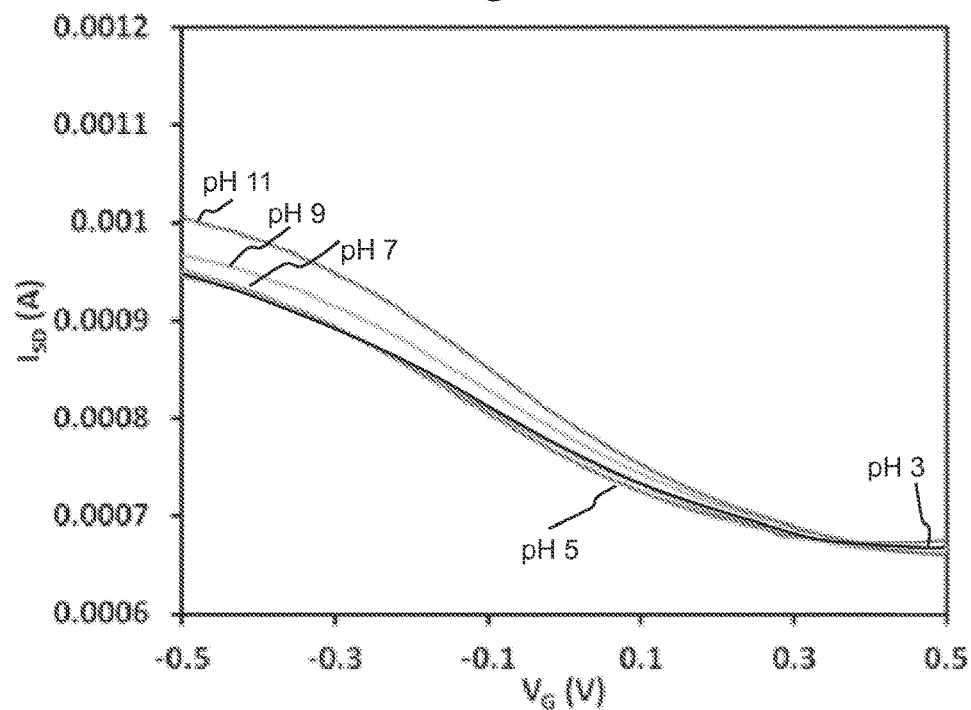
FIG. 3D illustrates FET characteristics for the system of FIG. 3C when exposed to various pH solutions.

Field-effect transistor (FET) measurements were taken to investigate the SWNT system response by passing a constant source drain voltage through the nanotube network ($V_{SD}$=50 mV) and measuring its current ($I_{SD}$) while sweeping the voltage applied through a liquid gate ($V_G$) as schematically illustrated in FIG. 3A. Those characteristics ($I_{SD}$ vs $V_G$) provide information about the semiconductor properties of systems 10. The gate was applied in solution through a Ag/AgCl reference electrode (liquid gating). FIG. 3B the manner in which these characteristics change from SWNT to SWNT/PAA to SWNT/PAA/Fe$_2$O$_3$ nanoparticles. FIG. 3C illustrates a plot of current versus time for a system hereof functionalized by dropcasting SWNTs, electropolymerizing PAA, and then dropcasting Fe$_2$O$_3$ nanoparticles without applying a gate voltage, when exposed to various pH solutions. FIG. 3D illustrates the FET characteristics for the same system when exposed to various pH solutions.

Figure 4:
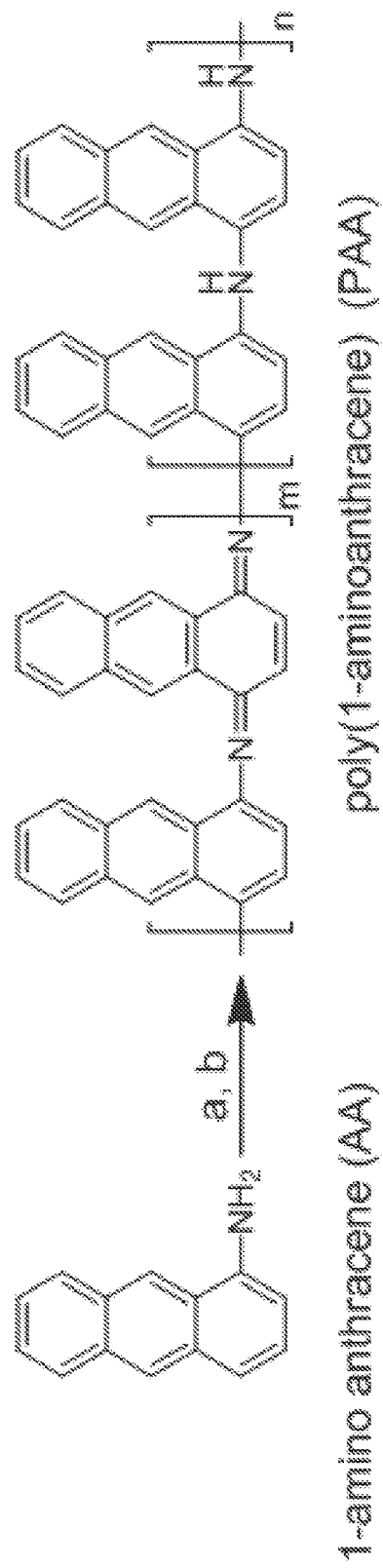
FIG. 4 illustrates a scheme for the synthesis of PAA polymer.

PAA polymer was synthesized following published procedures. See, for example, D. K. Moon, K. Osakada, T. Maruyama, K. Kubota and T. Yamamoto, *Macromolecules*, 1993, 26, 6992-6997. As illustrated in the scheme of FIG. 4, the AA monomeric units were homogenously dissolved in acetonitrile (MeCN), and with addition of H$_2$O$_2$ in the presence of catalytic FeSO$_4$. The brown solid PAA polymer was formed in 90% yield. The polymer was characterized using GPC indicating 198 averaging repeating units in the PAA polymer main chain. To study the interactions between PAA polymer and SWNTs as well as the response of the material to varying pH solutions, a solution of PAA in THF was spincast onto a network of previously deposited o-SWNTs. PAA is a polymer close in structure to polyaniline (PANi), having an anthracene group instead of benzene. For this reason it is expected that PAA and SWNT may have stronger interactions than PANi/SWNT as a result of π-π stacking, which can be observed through UV-Vis-NIR spectroscopy.

Figure 5A:
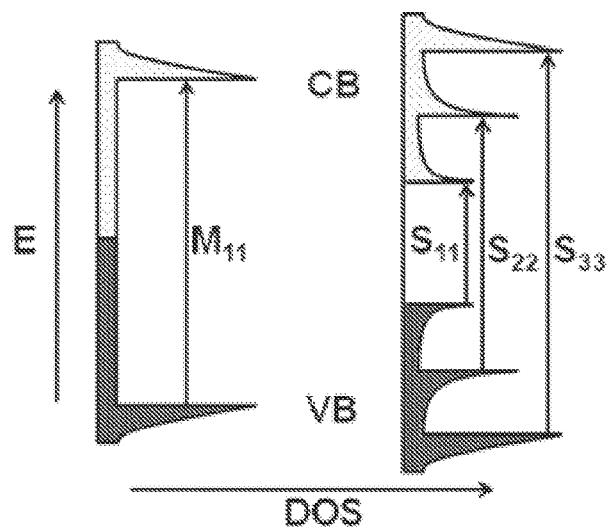
FIG. 5A illustrates a density of states (DOS) diagram of metallic and semiconducting SWNTs.
Figure 5B:
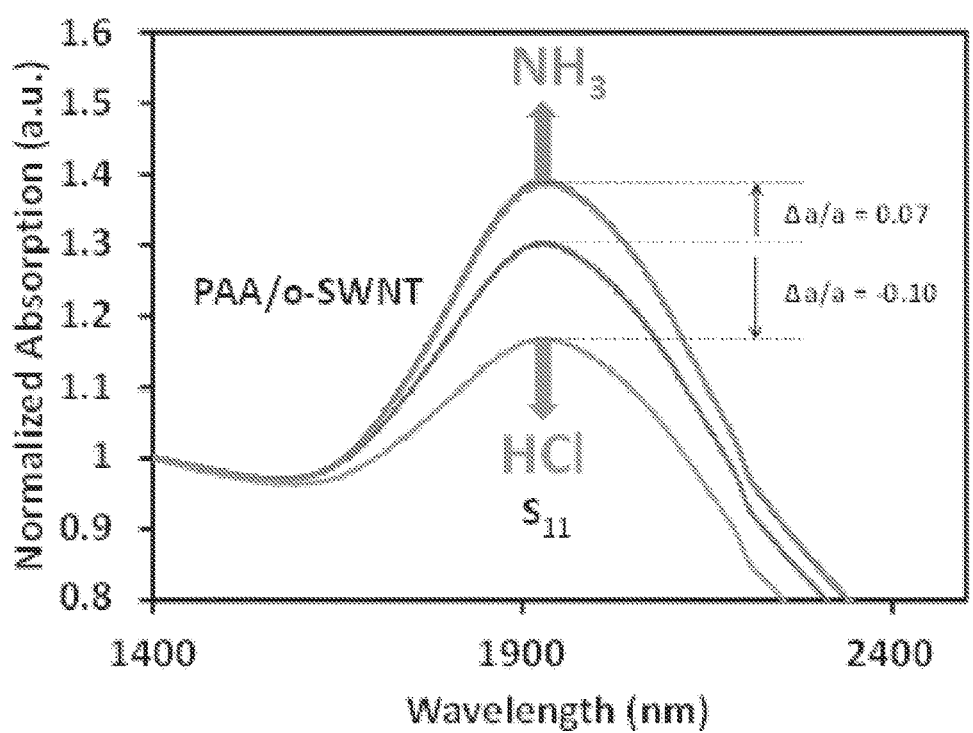
FIG. 5B illustrates the response of a system hereof including oxidized SWNT (o-SWNT) and immobilized PAA when exposed to $NH_3$ and HCl gas.
Figure 5C:
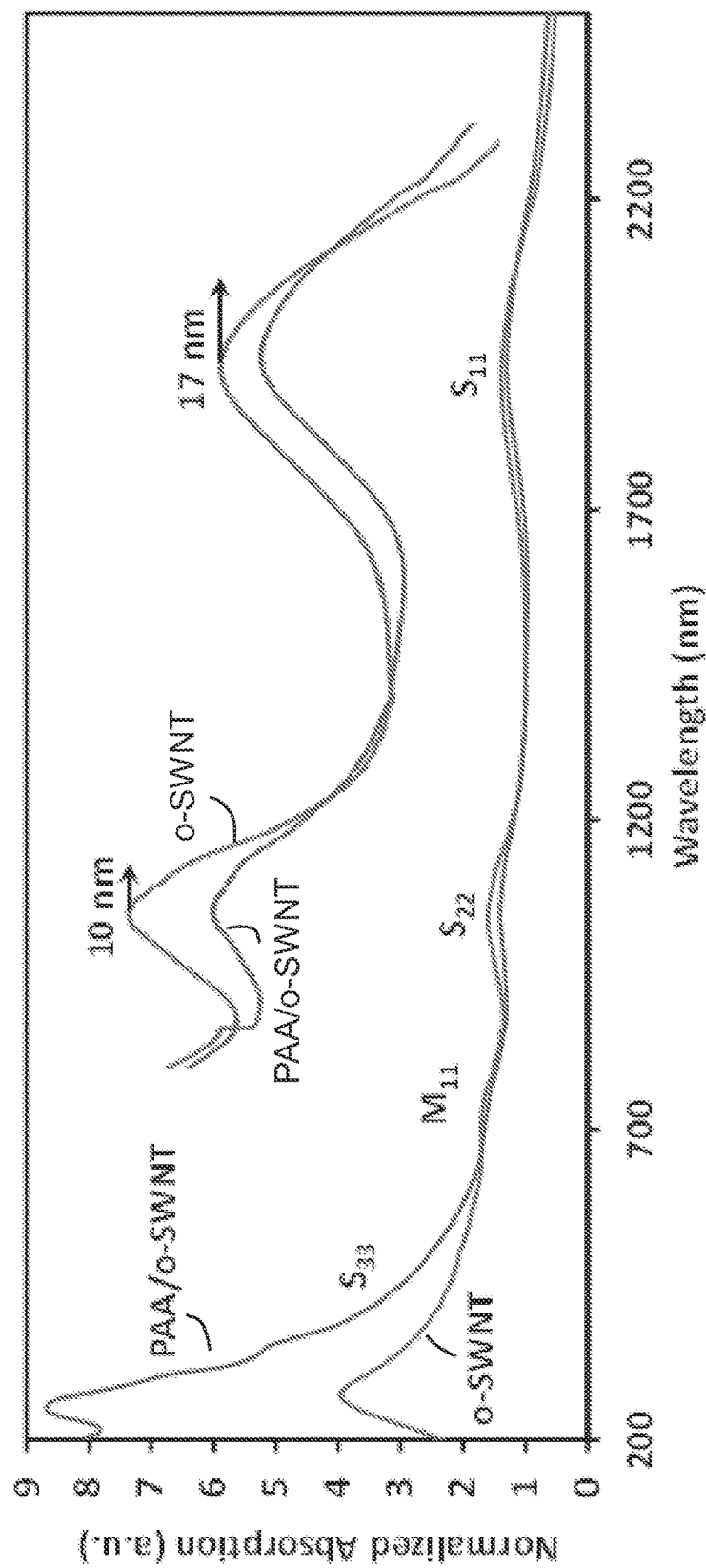
FIG. 5C illustrates the entire range of the UV-Vis-NIR absorption spectra of an o-SWNT film and a PAA/o-SWNT film, as well as the response of the PAA/o-SWNT film to acidic (HCl) and basic ($NH_3$) gases.

Using the above chemical synthesis method for preparing PAA, the optical properties of the PAA/o-SWNT were studied. UV-vis-NIR absorption spectroscopy was chosen to investigate the interaction of PAA polymer with o-SWNTs as well as the response of PAA/o-SWNT to acidic and basic vapors. UV-vis-NIR provides a useful technique to probe electron transfer in SWNTs, as SWNTs have a unique electronic structure with several van Hove singularities. A density of states (DOS) diagram of metallic and semiconducting SWNTs is depicted in FIG. 5A, showing the transition bands of the two types (metal and semiconductor) of SWNTs. Electron transitions between corresponding singularities in the valence band (VB) and the conduction band (CB) result in absorption bands observed in UV, visible and NIR regions of the electromagnetic spectrum (see FIG. 5B). A solid film was necessary to monitor the $S_{11}$ electronic transition, the most sensitive transition band, as it corresponds to the top of the valence band. The film was produced by first spraycoating o-SWNTs from a solution of dimethylformamide (DMF) onto a quartz plate followed by spincoat deposition of the polymer from a solution of tetrahydrofuran (THF). FIG. 3C shows the entire range of the UV-Vis-NIR absorption spectra of an o-SWNT film (blue), a PAA/o-SWNT film (red), and the response of the PAA/o-SWNT film to acidic (HCl) and basic gases (NH$_3$). A comparison of the optical properties o-SWNT film to that of the polymer coated film shows a distinct red shift in both the $S_{22}$ and $S_{11}$ electronic transitions. This shift is indicative of the attachments of PAA to the o-SWNT surface through noncovalent interactions. FIG. 5B illustrates the response of the systems exposed to NH$_3$ and HCl gas. A significant change in the intensity of the $S_1$ transition was observed for the exposure of such proton donating/withdrawing gases (Brønsted-Lowry acids/bases). In that regard, there was an increase in absorption for NH$_3$ gas and a decrease in absorption for HCl gas. Without limitation to any mechanism, a change in the $S_{11}$ transition band may be attributed to the amount of electrons added to or removed from the nanotube network. In that regard, a decrease in the $S_{11}$ absorbance (which corresponds to an increase in conductance) may be attributed to electrons being removed from the partially filled SWNT valence band. The system absorption recovers fully when HCl is purged and NH$_3$ reintroduced (see FIG. 5B).

Figure 6A:
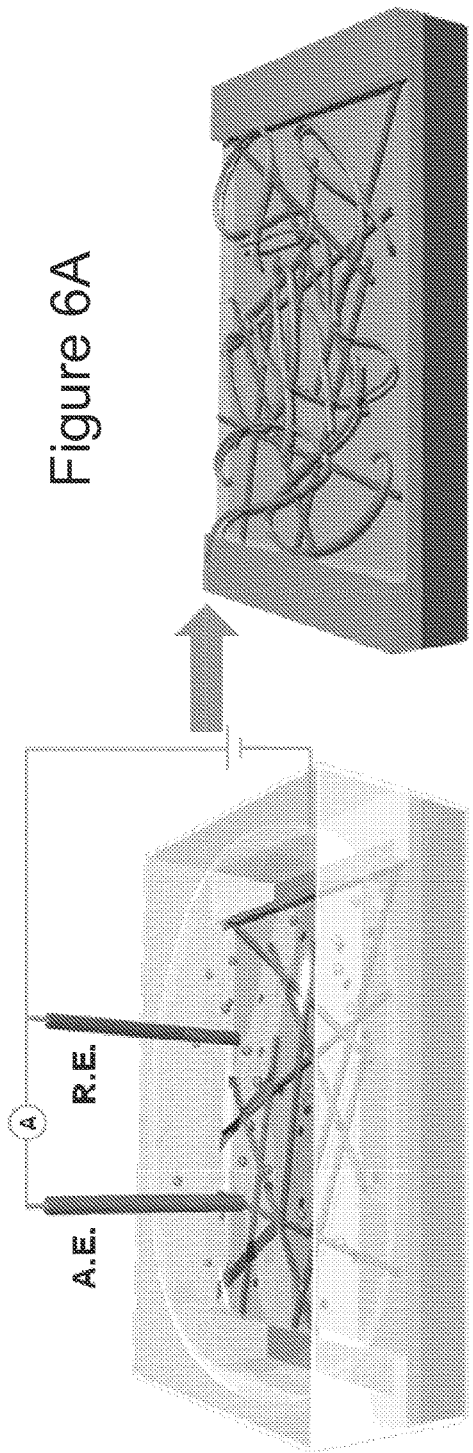
FIG. 6A illustrates a typical device setup for electropolymerization (EP) of aminoanthracene (AA) to poly(1-aminoanthracene) (PAA).
Figure 6B:
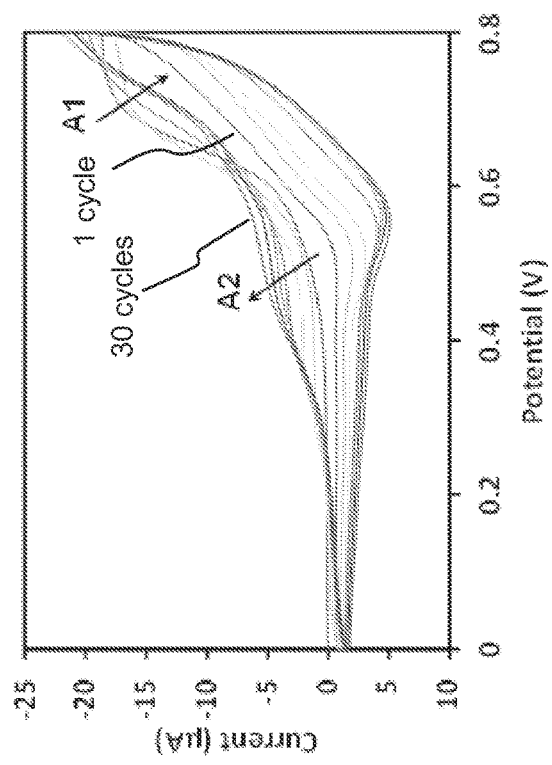
FIG. 6B illustrates a plot of current versus potential for the device of FIG. 6A during cyclic voltammetry (CV) cycle in formation of PAA.

Configuring a system hereof as a chemiresistor (which requires only a source and a drain terminal or electrode) allows for direct real-time electrical measurements of the system as a function of analyte as well as analyte concentration. As described above, a chemiresistor is a device that changes conductance/resistance upon exposure to an analyte of interest. Systems including PAA immobilized upon o-SWNT (PAA/o-SWNT) can, for example, easily be integrated into a chemiresistor system by depositing the functionalization layer on top of a Si/SiO$_2$ chip containing interdigitated gold electrode. FIG. 6A depicts a typical device setup for EP of aminoanthracene (AA) to poly(l-aminoanthracene) (PAA). The formation of PAA was confirmed by scanning electron microscopy (SEM). In this three electrode electrochemical cell, a network of oxidized single-walled carbon nanotubes (o-SWNTs) is used as the working electrode (W.E.). The potential of the W.E. is varied with respect to a quasi-reference electrode (R.E.) (Ag/AgCl), while the Pt wire auxiliary electrode (A.E.) is used to monitor the current produced without changing the potential of the R.E. By sweeping the potential of the working electrode while the system is submerged into an electrolyte solution (TBAP in MeCN) containing AA monomeric units, PAA is formed. More specifically by sweeping the potential between 0 to +0.8V at a sweep rate of 0.05 V/s, one cyclic voltammetry (CV) cycle is completed, and thus formation of PAA. The resulting current, plotted versus potential in FIG. 4C, tells us information about the EP process. With an increase in the number of cycles from 1 to 30 cycles, peaks for the oxidation of the monomeric unit (A1) disappear and a peak for dimer and oligomer units (A2) appears.

Figure 6C:
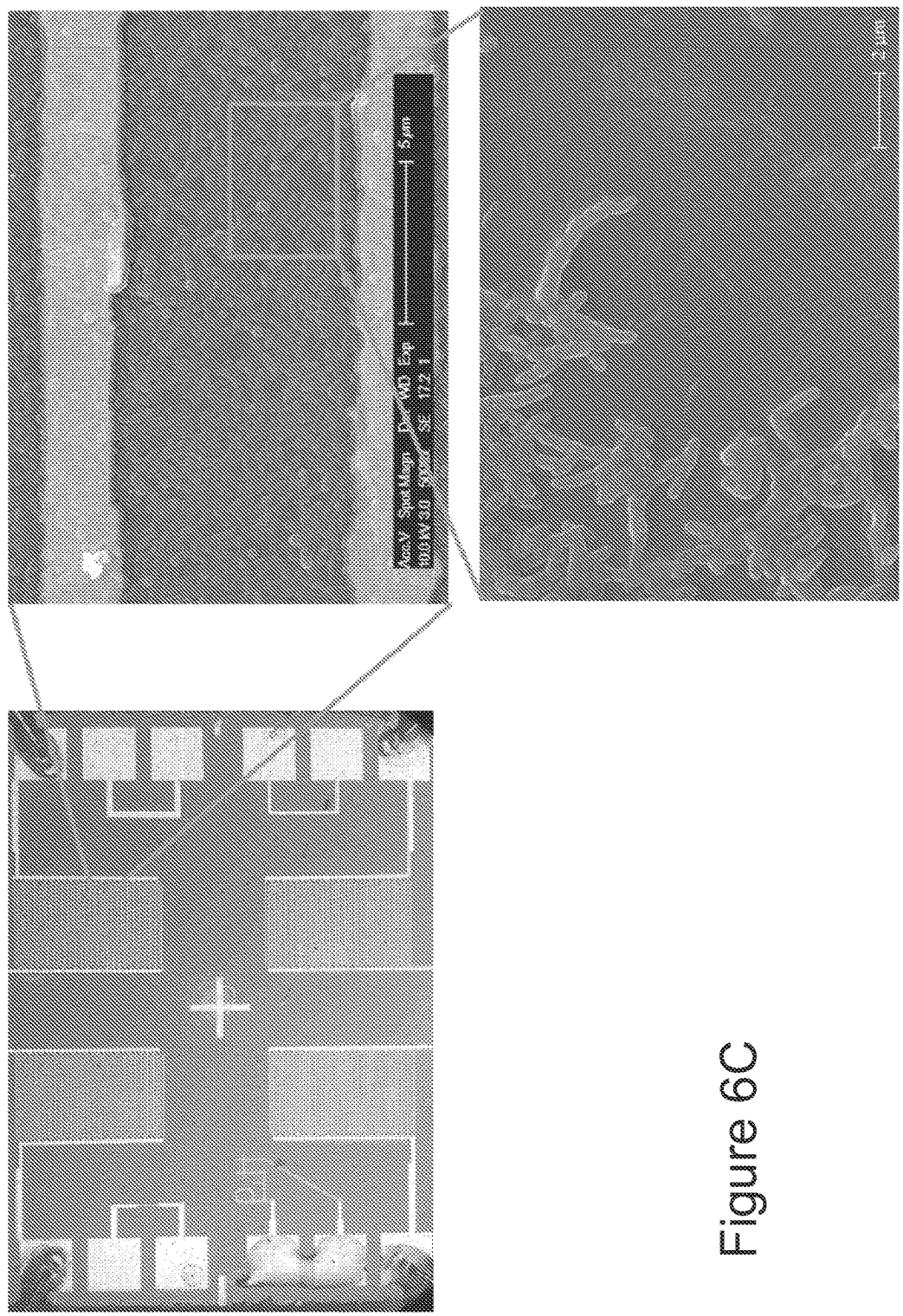
FIG. 6C illustrates an image of an EP prepared system hereof after 50 CV cycles, wherein the morphology of the polymer is illustrated photomicrographs.

An image of an EP prepared system after 50 CV cycles is given in FIG. 6C showing the morphology of the polymer. A higher magnification image (below) reveals o-SWNTs that are not connected to the nanotube network. Since these o-SWNTs were not connected to the working electrode or W.E. no polymer was deposited onto them. First, o-SWNTs in DMF are dropcast onto the chip and dried in ambient, followed by formation of PAA via electropolymerization (EP). By holding the voltage passing through the o-SWNT network ($V_{SD}$) constant and measuring the resulting current ($I_{SD}$) as a function of analyte, sensitivity of the chemiresistor to various analytes can be determined with relative ease. A Teflon flow cell was fabricated on top of the sensor device to facilitate the flow of various solutions over the system, while simultaneously maintaining a steady-state diffusion of hydronium ions.

Figure 7A:
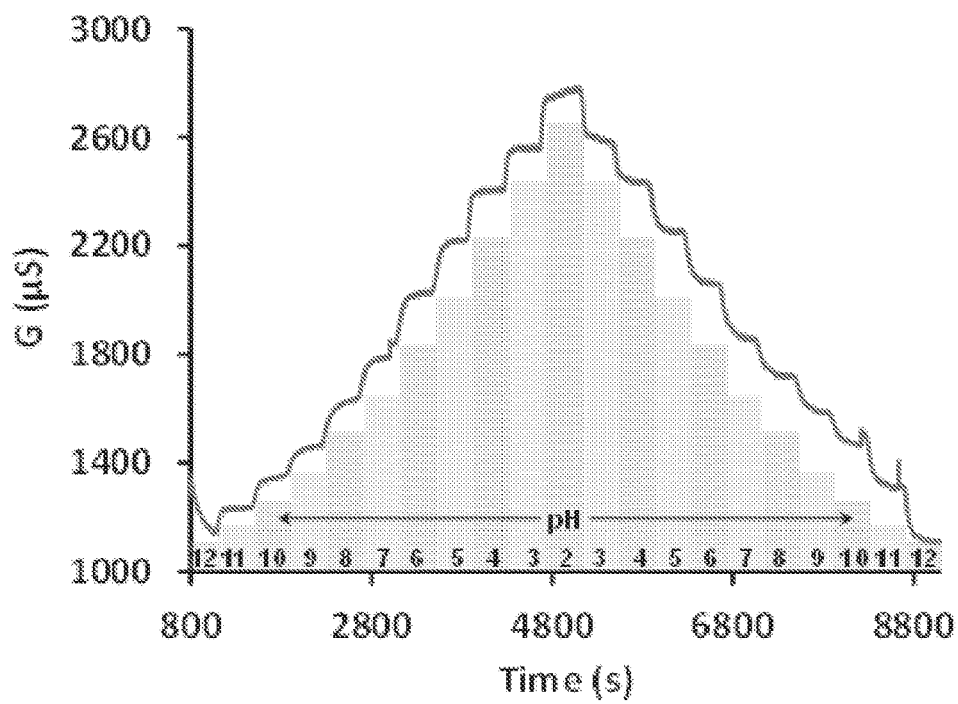
FIG. 7A illustrates a plot of conductance versus time for a PAA/o-SWNT system ($V_{SD}$) showing response to buffered solutions from pH=2 to pH=12.
Figure 7B:
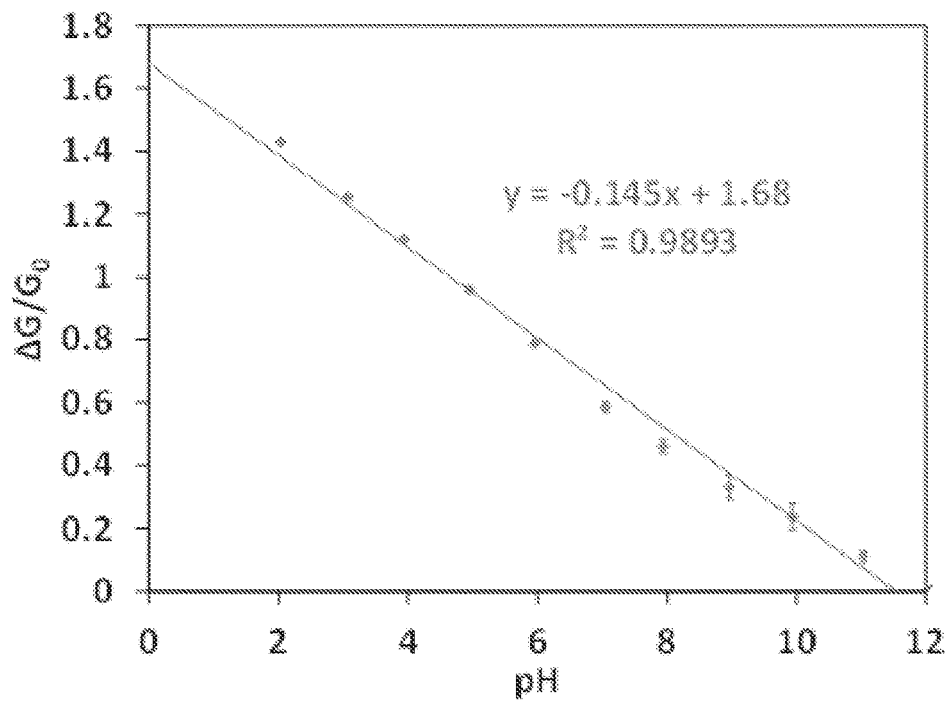
FIG. 7B illustrates a plot of relative response ($\Delta G/G_0$) of the system of FIG. 7A versus pH.
Figure 7C:
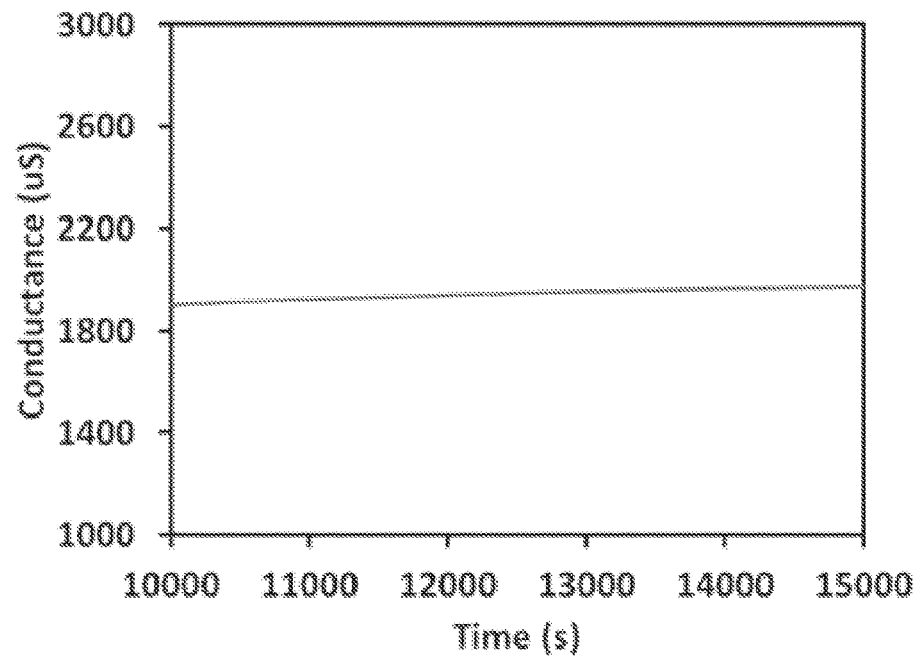
FIG. 7C illustrates a plot of conductance versus time for the system of FIG. 7A showing the stability of the system over a period of approximately two hours.
Figure 7D:
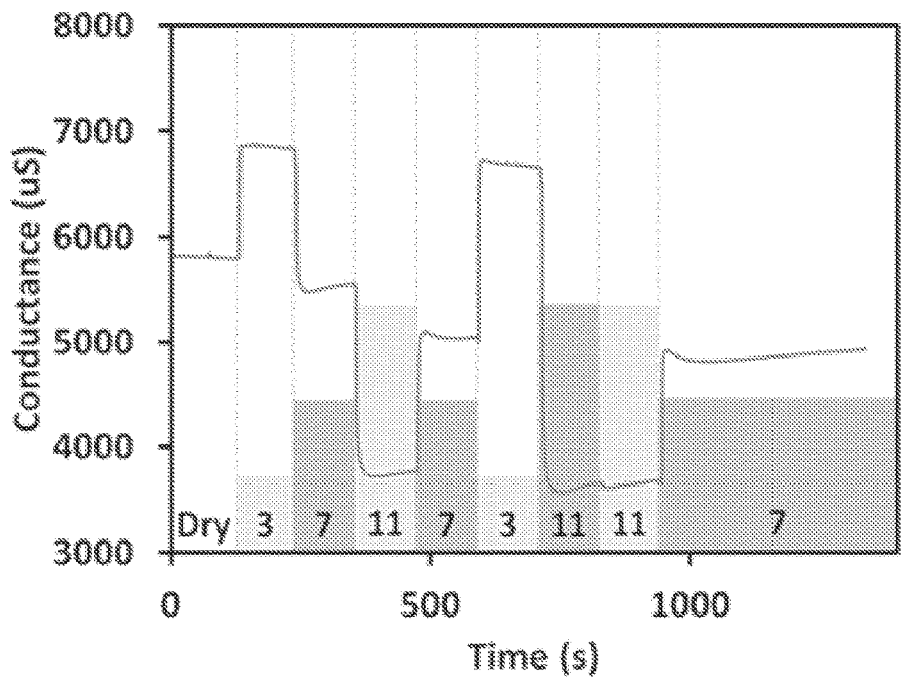
FIG. 7D illustrates conductance versus time for another system with a higher conductance range.
Figure 8A:
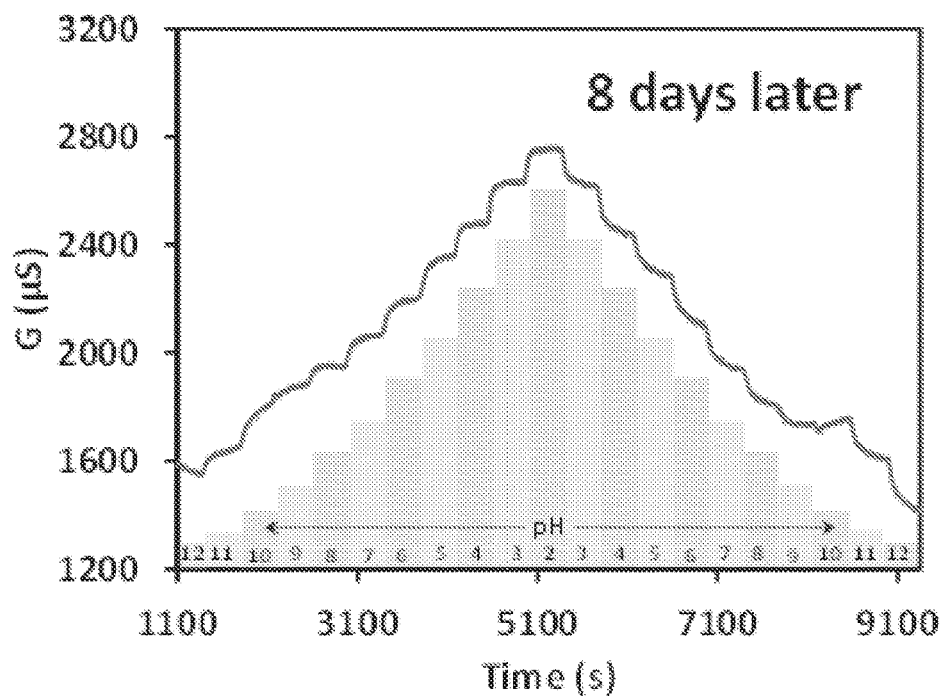
FIG. 8A illustrates relative response of the system of FIG. 7A as a function of time 8 days after fabrication and initial testing.
Figure 8B:
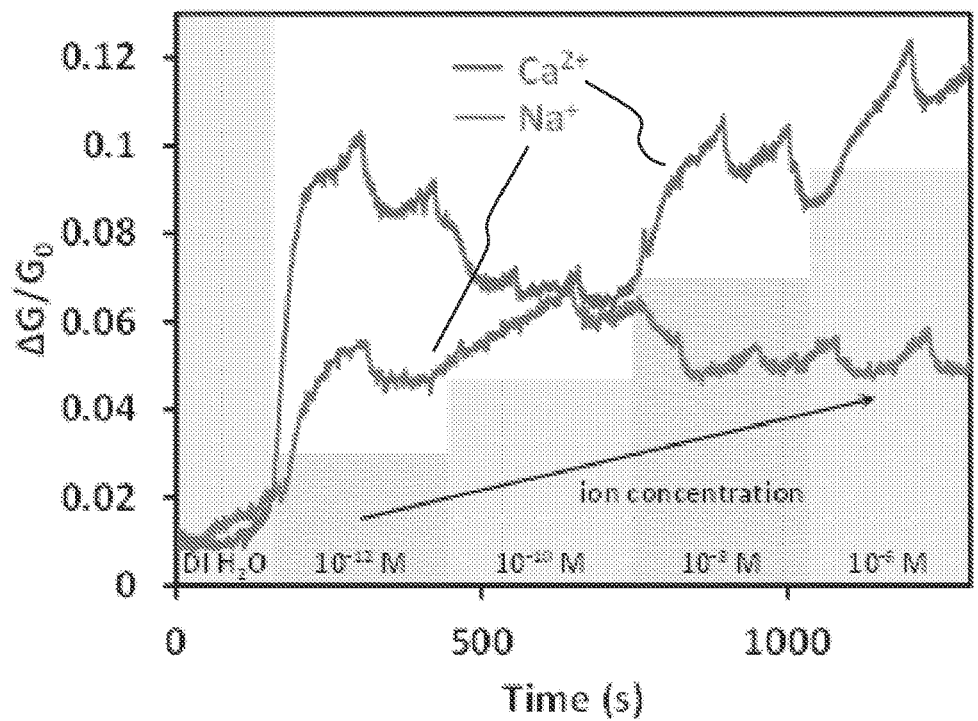
FIG. 8B illustrates relative response of the system of FIG. 7A as a function of time upon exposure to $Ca^{2+}$ and $Na^+$ ions as control analytes.
Figure 8C:
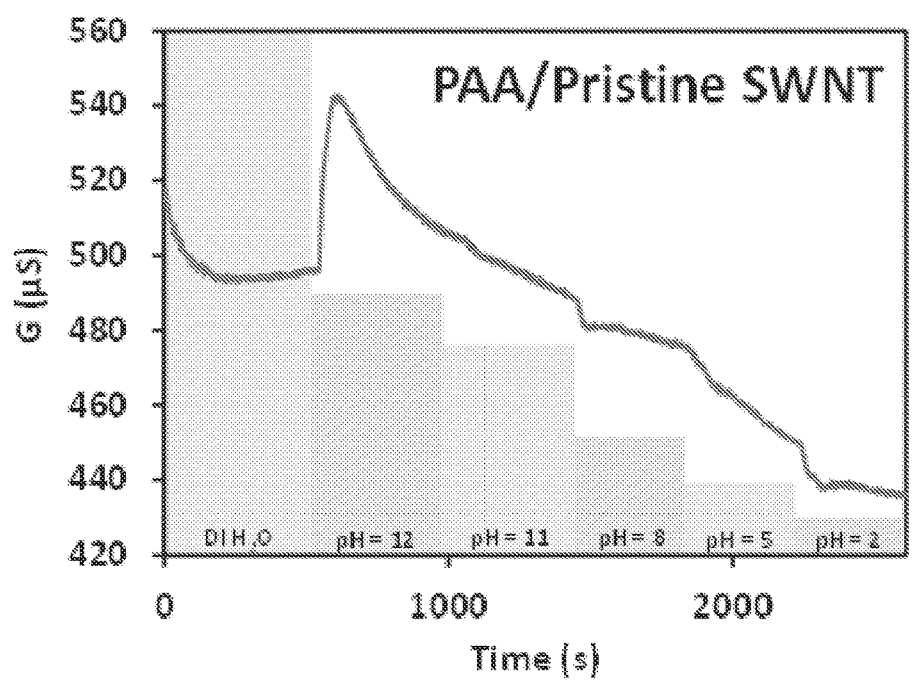
FIG. 8C illustrates the response of pristine SWNTs functionalizing with PAA via EP as a function of time.
Figure 8D:
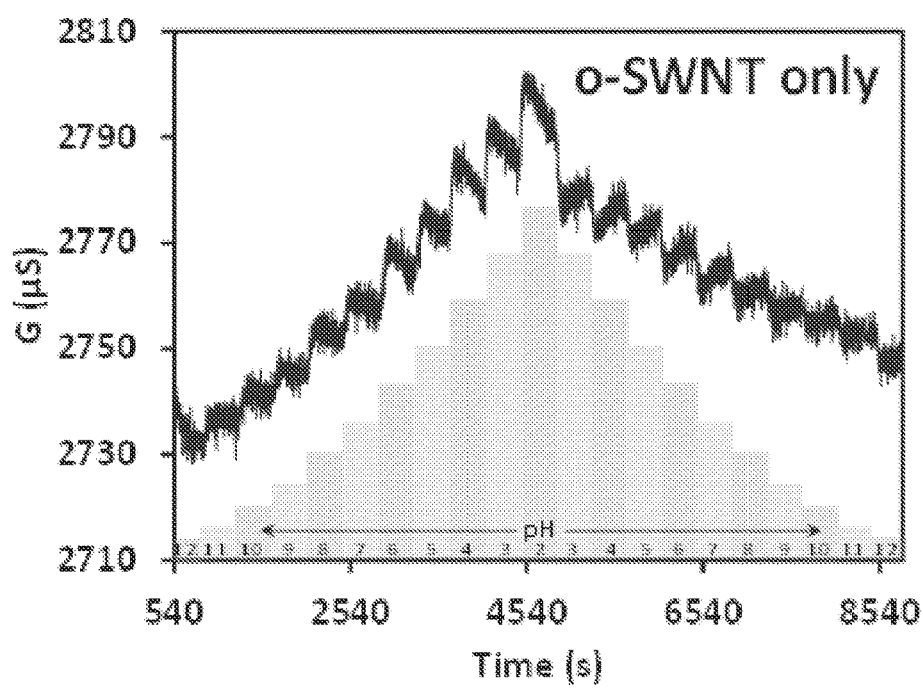
FIG. 8D illustrates the response of o-SWNTs with no functionalizing layer immobilized thereon as a function of time.

FIG. 7A illustrates a plot of conductance versus time for a PAA/o-SWNT device ($V_{SD}$) showing response to buffered solutions from pH=2 to pH=12. An increase in conductance was observed for increasing amounts of H$_3$O$^+$ ion (Brøn- sted-Lowry acid) which is in agreement with the optical measurements discussed above. Without limitation to any mechanism, increasing the amount of $H_3O^+$ ions in solution withdraws electrons from the partially filled SWNT VB, increasing the electrical conductivity. Furthermore, plotting the relative response ($\Delta G/G_0$) of the device versus pH (see FIG. 7B) reveals a linear calibration curve with very little variance ($R^2>0.99$). The scaling relationship between response and pH is desirable in the development of a sensor device, and the deviation between the response from 12 to 2 and that from 2 to 12 was minuscule (most error bars were smaller than the markers themselves). Additionally the stability of the system was good for more than two hours (see FIG. 7C). Testing another system with a higher conductance range revealed similar sensitivities (see FIG. 7D). The PAA coated o-SWNT electrodes were robust. As illustrated in FIG. 8A, 8 days after fabrication and initial testing, the system characteristics did not significantly degrade.

Control experiments were performed to further evaluate sensor performance and elucidate mechanisms of detection. To determine that the functionalization platform is specific to hydronium ions, $Ca^{2+}$ and $Na^+$ were tested as control analytes (see FIG. 8B). The PAA/o-SWNT system did not respond to concentrations of such ions in the range of $10^{-12}$ to $10^{-6}$ M, comparable to the range of concentrations of $H_3O^+$ ions tested. Pristine SWNTs functionalizing with PAA via EP resulted in a platform that was relatively insensitive to pH (see FIG. 8C), illustrating that oxidation of carbon SWNTs is desirable to increase sensitivity to pH. Without limitation to any mechanism, carboxylate groups on the surface of o-SWNT may be beneficial for attachment of the polymer to the nanotube via hydrogen bonding. Additionally, o-SWNT without the PAA layer are sensitive to pH. However, the response of o-SWNT without the PAA layer is relatively small (see FIG. 8D).

Experimental

Materials:

Pristine single-walled carbon nanotubes (P2-SWNTs) and oxidized SWNTs (P3) were purchased from Carbon Solutions, Inc. 1-aminoantracene (AA), anhydrous acetonitrile (MeCN), tetrabutylammonium perchlorate (TBAP), and $FeSO_4.7\ H_2O$ powder and were obtained from Sigma Aldrich. Buffered pH solutions were prepared through published methods from pH=1 to pH=13. The pH of the buffered solution was measured using a Mettler Toledo SevenMulti pH meter. The pH meter was calibrated with standard buffered solutions obtained from J. T. Baker.

Chemical Oxidative Polymerization of 1-Aminoanthracene (AA):

To a solution of AA (27 mg, 0.14 mmol) in $CH_3CN$ (8 mL), distilled water (8 mL) and sulfuric acid (68 μL, 1.2 mmol) were added dropwise. With the resulting solution was stirred at 30° C., $FeSO_4.7\ H_2O$ powder (1 mg, 3.6 μmol) was added, followed by the slow addition of 30% $H_2O_2$ (50 μL). The reaction mixture was stirred continuously for 48 hours under air at 30° C. to cause precipitation of a brown solid. After quenching with ice water, the solid was collected on a membrane filter and washed with methanol, 28% aqueous ammonia, and methanol again. The solid was then dried in vacuum at room temperature to give poly(l-aminoanthracene) (PAA) as a brown solid in 90% yield. Gel permeation chromatography (GPC) analysis using polystyrene standards in THF indicated that there are 198 average repeating units in the PAA polymer main chain ($M_w=3.8\times10^4$ g/mol and PDI=1.12). GPC was performed on a Waters Gel Permeation Chromatography system equipped with a Waters 510 HPLC pump, phenogel columns, and a Waters 410 Differential Refractometer at a flow rate of 0.4 mL/min.

Preparation of Conductive Carboxylated SWNTs:

SWNTs were dispersed in 20 mL of concentrated $H_2SO_4$/$HNO_3$ (3:1). The mixture was subsequently sonicated for 2 hrs at 40° C. in an ultrasonic bath (5510 Brasonic) to yield oxidized SWNTs (o-SWNTs) with lengths around 500 nm. Carboxylic acid groups were confirmed through FTIR spectroscopy. FT-IR spectra were recorded as thin film as KBr pellets on an Avatar 380 Nicolet FI-IR spectrometer. Upon completion, the mixture was added dropwise to 100 mL of cold distilled water and then filtered through 0.2-μm pore size PTFE (Teflon) laminated filter paper and then washed with water until no residual acid was present. In a number of embodiments, desirable loading of carboxylic groups (—COOH) on o-SWNTs was within the range of approximately 1-20 μmol/mg or within the range of approximately 10-15 μmol/mg. In a number of embodiments, loading of carboxylic groups was approximately 12 μmol/mg.

Sensor Device Fabrication:

Silicon chips with 300 nm thermal oxide layer and pre-fabricated interdigitated Au electrodes (MEMS and Nanotechnology Exchange) were wire-bonded into a 40-pin CERDIP package, followed by passivation of the system with epoxy (EPO-TEK, Epoxy Technology, MD USA). Aqueous suspensions (0.3 μL) of o-SWNTs in N,N-dimethylformamide (DMR) were dropcast onto the Si chips and allowed to dry in ambient. PAA was subsequently added to the o-SWNT network via Electropolymerization (EP) of the monomeric units, AA, into the polymer, PAA.[21] EP was performed with a using a CH instruments electrochemical analyzer with o-SWNTs configured as the working electrode in a three-electrode single compartment electrochemical cell. A platinum wire and a Ag/AgCl quasi-reference electrode were used as the auxiliary and reference electrodes, respectively. Anhydrous acetonitrile was used as the electrolyte solution which contained the supporting electrolyte, TBAP (0.1 M), and the monomeric units, AA (1 mM). PAA was prepared on the o-SWNT film using cyclic voltammetry by sweeping the electrode potential between 0 and +0.8 V at rate of 0.05 V/s. 24 hr prior to testing, the electrodes were conditioned in an aqueous solution containing a phosphate buffer (pH=5.60). The formation as well as morphology of PAA was characterized through scanning tunneling microscopy (SEM). SEM was performed on a Philips SL30 FEG microscope at an accelerating voltage of 10 keV.

Electrical Measurement:

For pH-solution sensing, devices fabricated as explained above were modified with a custom vial glued to the top of the package containing the chip. The devices were exposed to 500 μL of varying buffered pH solutions by dropcast. Conductance of the nanotube network was measured versus time while holding a constant voltage ($V_{SD}$) of 50 mV using a Keithley source meter. Field-effect transistor (FET) measurements were taken using two Keithly source meters. One to hold the constant bias voltage ($V_{SD}=50$ mV) and the other to sweep the gate voltage ($V_G=-0.75$ to 0.75V) through a Ag/AgCl reference electrode in buffered pH solutions.

Spectroscopic Measurement: UV-vis-NIR absorption spectra studies were taken by a Perkin-Elmer Lambda 900 UV-vis-NIR spectrophotometer. In the case of thin film measurements, an Iwata HP-BC Plus airbrush was used to spray a DMF suspension of o-SWNT onto a 1"×1" quartz plate at 180° C. PAA in THF was added to the SWNT network via spincoating and dried in ambient.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A system for measuring pH of an aqueous sample, comprising:
a substrate;
a sensor medium immobilized on the substrate, the sensor medium comprising a plurality of oxidized carbon nanostructures, wherein the plurality of oxidized carbon nanostructures is oxidized to provide a loading of carboxylic groups on the plurality of oxidized carbon nanostructures within the range of approximately 1-20 µmol/mg, and at least one composition selected from the group of a polymer including a group sensitive to H+ concentration and a metal oxide immobilized on the at least one oxidized carbon nanostructure, the at least one composition having at least one property that depends on pH of the aqueous sample;
a first conductive terminal in electrical connection with the sensor medium and a second conductive terminal in electrical connection with the sensor medium and spaced from the first conductive terminal;
at least one measurement system to measure an electrical property of the sensor medium, the measurement system being calibrated to determine and provide an output of pH of the aqueous sample from the measured electrical property.

2. The system of claim 1 wherein the at least one measurement system also measures at least one optical property of the sensor medium.

3. The system of claim 1 wherein the system operates as a chemiresistor.

4. The system of claim 1 wherein the at least one composition is immobilized on a network of single-walled carbon nanotubes.

5. The system of claim 1 wherein the plurality of oxidized carbon nanostructures is functionalized carboxylic groups having a carboxylic group loading the range of approximately 10-15 µmol/mg.

6. The system of claim 1 wherein the plurality of oxidized carbon nanostructures is functionalized with carboxylic groups to have a carboxylic group loading of approximately 12 µmol/mg.

7. The system of claim 1 wherein the polymer is a conductive polymer.

8. The system of claim 7 wherein the conductive polymer is a polyaminoanthracene, a polyaniline, a polypyrrole or a derivative thereof.

9. The system of claim 8 wherein the conductive polymer is a polyaminoanthracene.

10. The system of claim 7 wherein the at least one composition is immobilized on a network of single-walled oxidized carbon nanotubes.

11. The system of claim 10 wherein the plurality of oxidized carbon nanostructures are functionalized with carboxylic groups to have a loading of carboxylic groups within the range of approximately 12 µmol/mg.

12. The system of claim 10 wherein the plurality of oxidized carbon nanostructures are functionalized with carboxylic groups to have a carboxylic group loading within the range of approximately 10-15 µmol/mg.

13. The system of claim 1 wherein the polymer is poly (ethylene imine), sulfonated tetrafluoroethylene, or poly (sodium 4-styrenesulfonate).

14. The system of claim 1 wherein the polymer includes amine functional groups sensitive to H+ concentration.

15. The system of claim 1 wherein the polymer forms a proton exchange membrane.

16. The system of claim 1 wherein the at least one composition comprises a metal oxide.

17. The system of claim 1 wherein the composition comprises metal oxide nanoparticles.

18. The system of claim 17 wherein the metal oxide nanoparticles comprise at least one of $Fe_2O_3$, $Nd_2O_3$, $WO_3$, $TiO_2$, and $Al_2O_3$.

19. A method for measuring pH of an aqueous sample, comprising:
placing a system in fluid connection with the aqueous sample, the system comprising a substrate and a sensor medium immobilized on the substrate, the sensor medium comprising a plurality of oxidized carbon nanostructures, wherein the plurality of oxidized carbon nanostructures is oxidized to provide a loading of carboxylic groups on the plurality of oxidized carbon nanostructures within the range of approximately 1-20 µmol/mg, and at least one composition selected from the group of a conductive polymer including a group sensitive to H+ concentration and a metal oxide immobilized on the at least one oxidized carbon nanostructure, and a first conductive terminal in electrical connection with the sensor medium and a second conductive terminal in electrical connection with the sensor medium and spaced from the first conductive terminal, the at least one composition having at least one property that depends on pH of the aqueous sample;
measuring at least one electrical property of the sensor medium;
relating a measured value of the at least one electrical property of the sensor medium to pH via a predetermined calibration of the measured electrical property of system for pH; and
providing an output of the pH.

* * * * *